United States Patent
Cutforth et al.

(10) Patent No.: US 11,967,085 B2
(45) Date of Patent: Apr. 23, 2024

(54) IMAGE DATA PROCESSING METHOD AND APPARATUS

(71) Applicant: CANON MEDICAL SYSTEMS CORPORATION, Otawara (JP)

(72) Inventors: Murray Cutforth, Edinburgh (GB); Ewan Hemingway, Edinburgh (GB)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 352 days.

(21) Appl. No.: 17/173,764

(22) Filed: Feb. 11, 2021

(65) Prior Publication Data
US 2022/0254032 A1 Aug. 11, 2022

(51) Int. Cl.
*G06T 7/20* (2017.01)
*A61B 5/00* (2006.01)
(Continued)

(52) U.S. Cl.
CPC ............... *G06T 7/20* (2013.01); *A61B 5/055* (2013.01); *A61B 5/7267* (2013.01); *A61B 8/06* (2013.01); *A61B 8/0891* (2013.01); *A61B 8/488* (2013.01); *G06T 7/0012* (2013.01); *G06T 7/13* (2017.01); *G06T 7/143* (2017.01); *G06T 2207/10092* (2013.01); *G06T 2207/10132* (2013.01); *G06T 2207/20081* (2013.01); *G06T 2207/20084* (2013.01); *G06T 2207/30104* (2013.01)

(58) Field of Classification Search
CPC ........... G06T 7/20; G06T 7/0012; G06T 7/13; G06T 7/143; G06T 2207/10092; G06T 2207/10132; G06T 2207/20081; G06T 2207/20084; G06T 2207/30104; A61B 5/055; A61B 5/7267; A61B 8/06; A61B 8/0891; A61B 8/488; A61B 5/0263
See application file for complete search history.

(56) References Cited

U.S. PATENT DOCUMENTS

2012/0232853 A1* 9/2012 Voigt ..................... G16H 50/50
703/11
2012/0265075 A1* 10/2012 Pedrizzetti ............... A61B 8/06
600/454

(Continued)

FOREIGN PATENT DOCUMENTS

WO WO 2018/013247 A2 1/2018

OTHER PUBLICATIONS

Raissi, M., et al., "Hidden Fluid Mechanics: A Navier-Stokes Informed Deep Learning Framework for Assimilating Flow Visualization Data", Retrieved from the internet: https://arxiv.org/pdf/1808.04327.pdf, Aug. 20, 2018, pp. 1-33.

(Continued)

*Primary Examiner* — Jon Chang
(74) *Attorney, Agent, or Firm* — Oblon, McClelland, Maier & Neustadt, L.L.P.

(57) ABSTRACT

A medical image processing apparatus including processing circuitry configured to: obtain from medical imaging measurements, observations of one or more vector or tensor valued fields as projected from one or more 2D acquisition planes; use an optimisation procedure to determine from the observations a superset of 3D fields (which may be scalar, vector, or tensor) via a solution ansatz constrained by a system of partial differential equations, and output the plurality of these fields.

20 Claims, 5 Drawing Sheets

(51) Int. Cl.
*A61B 5/055* (2006.01)
*A61B 8/06* (2006.01)
*A61B 8/08* (2006.01)
*G06T 7/00* (2017.01)
*G06T 7/13* (2017.01)
*G06T 7/143* (2017.01)

(56) References Cited

U.S. PATENT DOCUMENTS

2013/0338496 A1  12/2013  Hielscher et al.
2015/0286785 A1  10/2015  Hielscher et al.
2020/0074664 A1*  3/2020  Weber .................... G06T 17/00

OTHER PUBLICATIONS

Prince, J.L., "Tomographic Reconstruction of 3-D Vector Fields", Department of Electrical and Computer Engineering, IEEE, 1993, pp. V-483 ~ V-486.
Papadaniil, C.D., et al., "Tomographic Reconstruction of 3-D Irrotational Vector Fields via a Discretized Ray Transform" Journal of Mathematical Imaging and Vision, Jan. 2015, 18 pages with cover page.
Ingmar Voigt et al., Patient-Specific Model of Left Heart Anatomy, Dynamics and Hemodynamics from 4D Tee: A First Validation Study; Springer-Verlag Berlin Heidelberg 2011, pp. 341-349.
Ingmar Voigt et al., Robust Physically-Constrained Modeling of the Mitral Valve and Subvalvular Apparatus; Springer-Verlag Berlin Heidelberg 2011, pp. 504-511.

* cited by examiner

IMAGE DATA PROCESSING METHOD AND APPARATUS

FIELD

Embodiments described herein relate generally to an apparatus and method for image data processing, for example processing image data in order to determine 3D data fields.

BACKGROUND 3D medical imaging data can be obtained using a range of medical imaging modalities. Determining 3D data fields from medical imaging data can present challenges in speed of data processing and data collection. Furthermore, the collected data can in certain circumstances be noisy and effective noise reduction techniques are desirable. In addition, it could be beneficial if additional properties or measurements can be determined. Furthermore, certain medical imaging modalities may not be suited to 3D imaging.

BRIEF DESCRIPTION OF THE DRAWINGS

Embodiments are now described, by way of non-limiting example, and are illustrated in the following figures, in which.

DETAILED DESCRIPTION

Certain embodiments provide medical image processing apparatus comprising processing circuitry configured to receive measured 2D physical quantity data; determine 3D physical quantity data from the 2D physical quantity data using a model trained to transform 2D physical data into 3D physical data, the model being constrained by a system of equations representative of a physical model describing underlying physical properties.

Certain embodiments provide a medical imaging method comprising receiving measured 2D physical quantity data; and determining 3D physical quantity data from the 2D physical quantity data using a model trained to transform 2D physical data into 3D physical data, the model being constrained by a system of equations representative of a physical model describing underlying physical properties.

Figure 1:
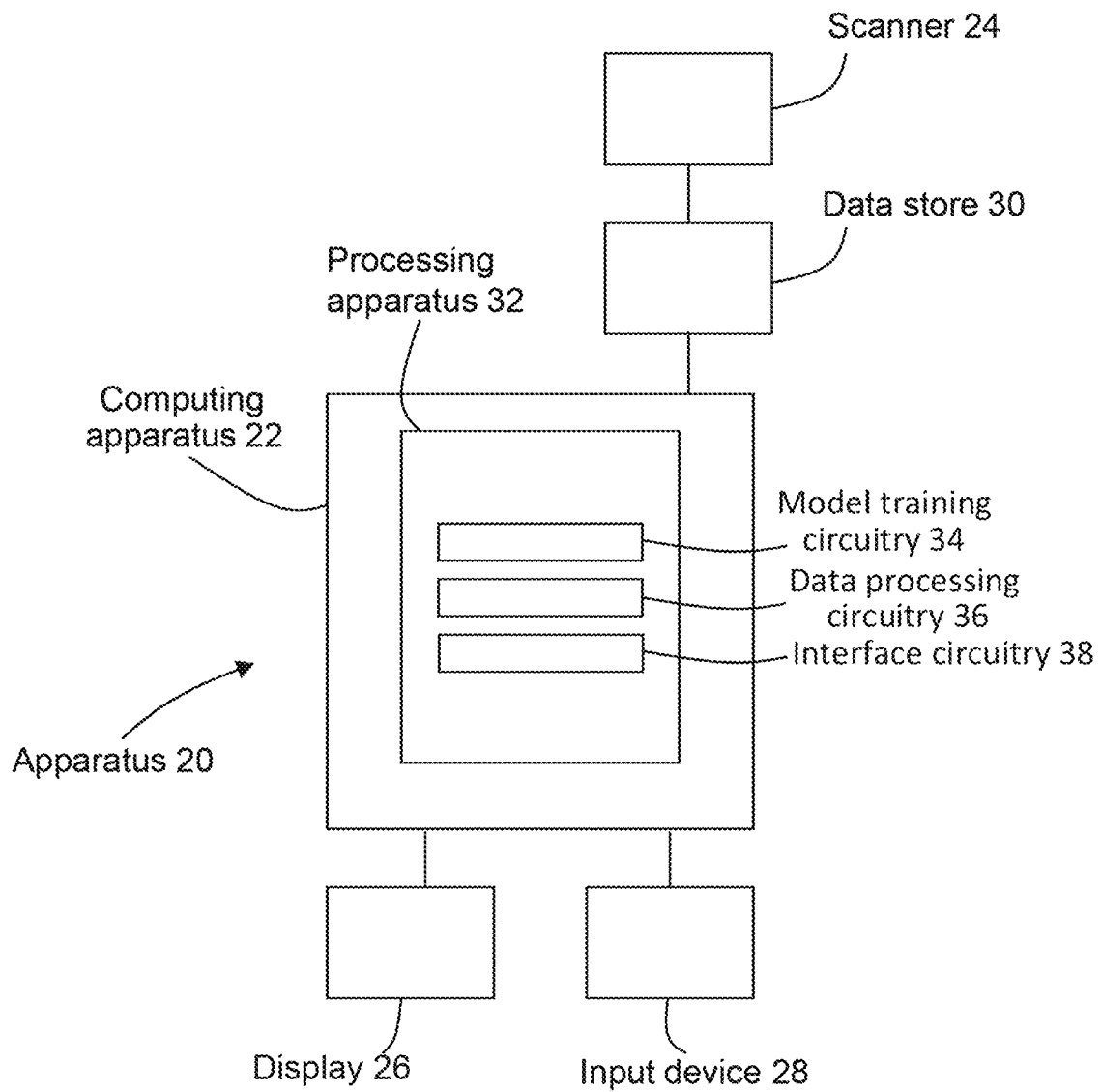
FIG. 1 is a schematic illustration of an apparatus in accordance with an embodiment.

A data processing apparatus 20 according to an embodiment is illustrated schematically in FIG. 1. In the present embodiment, the data processing apparatus 20 is configured to obtain 2D medical imaging data in one or more acquisition planes. In other embodiments, the data processing apparatus 20 can be configured to process any appropriate data, but in this example processes medical imaging data.

The data processing apparatus 20 comprises a computing apparatus 22, which in this case is a personal computer (PC) or workstation. The computing apparatus 22 is connected to a display screen 26 or other display device, and an input device or devices 28, such as a computer keyboard and mouse.

The computing apparatus 22 is configured to obtain image data sets from a data store 30. The image data sets are generated by processing data acquired by a medical imaging scanner 24 and stored in the data store 30.

The scanner 24 can be configured to generate the 2D medical imaging data in the one or more acquisition planes in any imaging modality. For example, the scanner 24 may comprise an ultrasound scanner, magnetic resonance (MR or MRI) scanner, CT (computed tomography) scanner, conebeam CT scanner, X-ray scanner, PET (positron emission tomography) scanner or SPECT (single photon emission computed tomography) scanner or the like. Some specific examples of scanner 24 include a 2D Doppler ultrasound scanner, a phase-contrast MRI scanner, a scanner for performing ultrasound elastography, and a scanner for performing diffusion tensor imaging, amongst others.

The computing apparatus 22 optionally receives medical image data from one or more further data stores (not shown) instead of or in addition to data store 30. For example, the computing apparatus 22 could receive medical image data from one or more remote data stores (not shown) which may form part of a Picture Archiving and Communication System (PACS) or other information system.

Computing apparatus 22 comprises a processing apparatus 32 for automatically or semi-automatically processing medical image data. The processing apparatus 32 comprises model training circuitry 34 configured to train one or more models; data processing circuitry 36 configured to apply trained model(s) to obtain one or more 3D fields for example for output to a user or for use in determining one or more clinically relevant properties, that can be output to a user; and interface circuitry 38 configured to obtain user or other inputs and/or to output results of the data processing.

In the present embodiment, the circuitries 34, 36, 38 are each implemented in computing apparatus 22 by means of a computer program having computer-readable instructions that are executable to perform the method of the embodiment. However, in other embodiments, the various circuitries may be implemented as one or more ASICs (application specific integrated circuits) or FPGAs (field programmable gate arrays). The computing apparatus 22 also includes a hard drive and other components of a PC including RAM, ROM, a data bus, an operating system including various device drivers, and hardware devices including a graphics card. Such components are not shown in FIG. 1 for clarity.

The data processing apparatus 20 of FIG. 1 is configured to perform methods as illustrated and/or described in the following.

Figure 2:
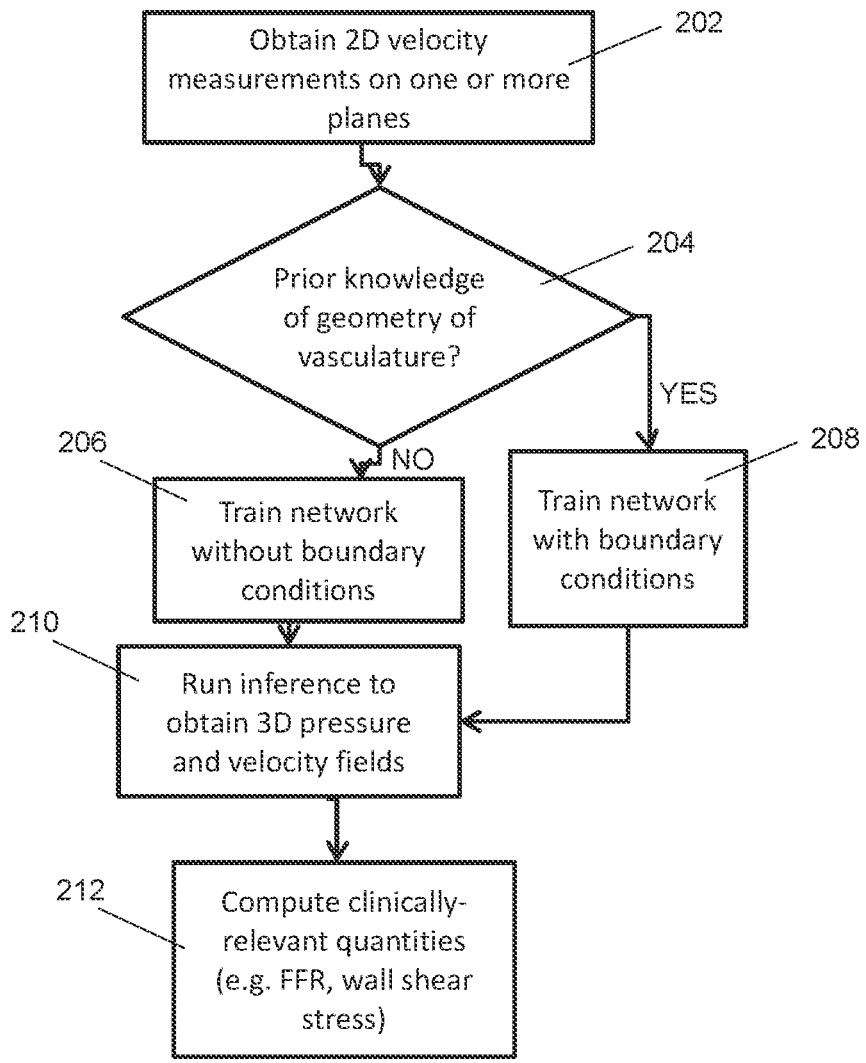
FIG. 2 is a flowchart illustrating a process of determining clinically relevant quantities from 3D fields determined from 2D measurements.

A process of determining clinically relevant quantities from 3D fields determined from 2D measurements is illustrated in FIG. 2.

In step 202, measurements of one or more vector or tensor valued fields projected onto one or more 2D acquisition planes through a target are obtained by medical imaging measurements, such as measurements using the scanner 24. As noted above, the scanner 24 could be, for example, a 2D Doppler ultrasound scanner or a phase-contrast MRI scanner, amongst others. Often such 2D measurements can be collected quickly and/or with less computational resource, relative to directly collecting 3D measurements. In an example, the measurements comprise velocity measurements such as velocity of fluid flowing in a vessel, but are not limited to this.

A solution ansatz, that comprises and utilizes a model, is initialized to determine a superset of 3D data fields (which may be scalar, vector, or tensor) from the observations. In examples, the 3D fields may be representative of pressure and velocity, but other properties could be determined. In this example, the solution ansatz is a neural network (i.e. the model is in the form of a neural network) and the following description refers to a neural network but other forms of solution ansatz could be used and could be substituted or interchanged with the neural network in the following description.

The neural network is a physics-informed neural network that is trained (e.g. by the model training circuitry 34 shown in FIG. 1) by minimising differences between the predictions of the neural network and the measurements of the one or more vector or tensor valued fields projected onto one or more 2D acquisition planes through the target. For example, once the neural network makes a prediction of a 3D data field comprising a property (e.g. velocity) whose projection on the 2D acquisition plane is measured, then the components of the 3D data field that are out of the 2D acquisition plane can be determined and subtracted from the 3D data field predicted using the neural network to obtain a predicted projection on the 2D acquisition plane. The neural network is trained by optimised parameters of the neural network by minimising this difference between the predicted and measured projections onto the one or more 2D acquisition planes using suitable techniques, such as minimising an error or cost function. However, although the above is given as a particularly beneficial and convenient example, other neural network optimization techniques could be used.

The training of the neural network optionally comprises using boundary conditions. At step 204, if there is any prior knowledge of the target, for example of the geometry or segmentation of the target, then this can be used to set boundary conditions for training the neural network, step 208. If prior knowledge of the system is not available, then the solution ansatz (e.g. neural network) can be trained Without boundary conditions, step 206. In an example, the prior knowledge can be obtained using another imaging technique, such as B-mode (i.e. brightness mode) ultrasound imaging, which can be used to identify physical boundaries, such as vessel boundaries, that are then used to set the boundary conditions in the training of the neural network. The measurements of the one or more vector or tensor valued fields projected onto the one or more 2D acquisition planes through the target can be obtained using a different technique or modality, such as 2D Doppler ultrasound measurements, to the technique or modality used to determine the boundaries (e.g. B-mode ultrasound imaging).

As noted above, the solution neural network is a physics informed neural network that is constrained by equations representative of a physical model that describes the physical properties of the target or an underlying physical process occurring at the target. However, as noted above, whilst a physics informed neural network is particularly beneficial and convenient, another type of physics informed solution ansatz could be used. The equations representative of the physical model used to constrain the neural network can comprise partial differential equations.

In one possible but not exhaustive example, the solution neural network is constrained to obey the equations representative of the physical model (e.g. in the form of one or more differential equation or partial differential equations) using an additional loss function that is representative of a degree by which the output of the neural network disobeys the equations representative of the physical model. This additional loss function can be constructed, for example, by combining derivatives of the neural network in such a way that they will sum to zero if the solution obeys the governing equations representative of the physical model. However, as noted above, this approach is not exhaustive and alternative approaches for implementing the constraints based on physical properties or underlying physical process at the target may be evident to a skilled person based on the teaching in this specification.

In examples, the underlying physical process is fluid flow, such as arterial blood flow. For measuring properties of fluid flow, the Navier-Stokes equations or a reduced order approximation to the Navier-Stokes equations could be used to constrain the training of the neural network. The Navier-Stokes equations are a series of partial differential equations that describe the motion of viscous substances, such as blood or oil. The solution of the Navier-Stokes equations is a vector field representing flow velocity, accompanied by equations of state that relate properties such as pressure, temperature and density. Other physical properties such as pressure and temperature can be determined from the flow velocity vector field.

Once the neural network has been trained and the parameters of the neural network optimized, in step 210 the neural network can be used to infer the superset of 3D data fields from the measurements of the one or more vector or tensor valued fields projected onto the one or more 2D acquisition planes through the target obtained in step 202. In examples, a line integral or point estimate of the fields can be obtained. In the specific examples described above, the 3D fields comprise 3D fluid velocity and pressure but other properties such as temperature or density could be determined. This processing of the measurements of the one or more vector or tensor valued fields projected onto the one or more 2D acquisition planes through the target using the trained neural network to determine the superset of 3D data fields could be carried out, for example, by the data processing circuitry 36 shown in FIG. 1.

The superset of 3D fields can then be output directly and/or the 3D fields can be used to determine clinical values in step 212 that can be output, for example on the display screen 26, written to a log or data storage or provided via another form of output.

This output may be carried out, for example, by the interface circuitry 38 of FIG. 1. For example, the 3D fields may comprise at least one of: velocity and/or pressure, and the clinical values may comprise clinically useful derived quantities involving the pressure, such as one or more of: fractional flow reserve (FFR), shear wall stress and/or the like. The output could be in the form of a 3D image or selectable cross sections through the target, or other suitable representation. In examples, the 3D fields or the clinical data can be used as, or to set, the boundary and/or initial conditions of a conventional fluid dynamics solver.

Figure 3:
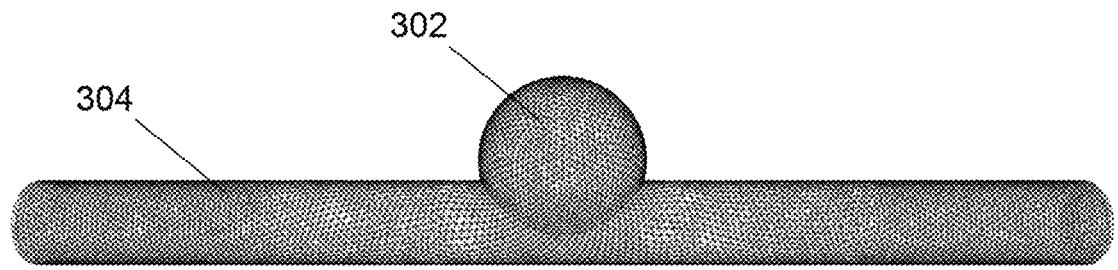
FIG. 3 shows an example aneurysm geometry for illustrating an application of the method of FIG. 2.
Figure 4:
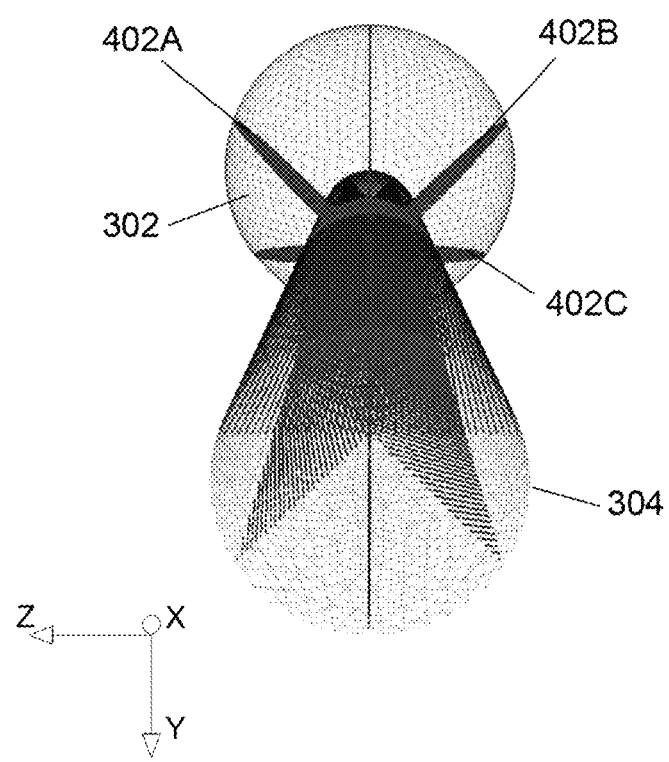
FIG. 4 is a perspective view of the example aneurysm geometry of FIG. 3 showing 2D acquisition planes.

A specific example of the application of the process of FIG. 2 is illustrated with respect to FIGS. 3 to 6. FIG. 3 shows a model of an aneurysm 302 in a blood vessel 304. As shown in FIG. 4, 2D Doppler ultrasound measurements are taken, e.g. using the scanner 24 in FIG. 1, in one or a plurality of 2D planes 402A-C through the blood vessel 304 and aneurysm 302. In this way, only projections of fluid (i.e. blood) velocity projected onto the 2D planes 402A-C are obtained. In alternate examples, the 2D measurements can be taken using phase-contrast MRI or any other suitable imaging technique. These velocity measurements of fluid velocity projected onto the 2D planes 402A-C through the blood vessel 304 and aneurysm 302 can be of the form:

$$[x_i, y_i, z_i, t_i, a_i, b_i, C_i, \hat{n}_i]_{i=1}^{N_0}$$

where x, y, z are position coordinates; a, b, c are in-plane velocity components in a reference (Cartesian) coordinate system, and $\hat{n}_i$ is the normal vector.

A neural network is initialized, which predicts pressure and velocity at each space-time coordinate. The operation of the neural network can be represented by:

$$(x, y, z, t) \mapsto (u, v, w, p) \text{ for } x, y, z \in \mathbb{R}^3 \times [0, T]$$

The neural network is a physics-informed neural network that is constrained by equations representative of an underlying physical model, in this case an arterial blood flow model in which the domain is fixed. However, in an otherwise similar alternative embodiment, the domain deforms with time. In this example, the fluid flow in the blood vessel is governed by the Navier-Stokes equations, which are in turn used to constrain the neural network. However, it will be appreciated that in other applications different sets of differential equations representative of the physical model underlying a process could be used.

As noted above, the solution of the Navier-Stokes equations is a vector field representing flow velocity. Out-of-plane velocity components can be subtracted from the velocity predictions of the neural network (u) to fit the velocity predictions of the neural network (u) to the projected observations (a), i.e.:

$$a = u - (u, \hat{n})\hat{n}$$

Minimization of an error or cost function such as standard mean squared error loss, or other optimization technique, can be used to train the neural network to minimize the difference with the projected observations, whilst obeying and being constrained by the equations representing the underlying physical model of the target, in this case the Navier-Stokes equations.

As indicated in step 208 of FIG. 2, if prior knowledge of the target (in this case the location, geometry and extent of the blood vessel 304 and aneurysm 302) is known, then this can be used to apply boundary conditions to the training of the neural network, which can improve accuracy. For example, the prior knowledge may comprise segmentation or other data that indicates physical boundaries of the target. In an example, the boundary information comprises information regarding the boundaries or vessel walls of the blood vessel 304 and aneurysm 302 determined using B-mode ultrasound.

Figure 5:
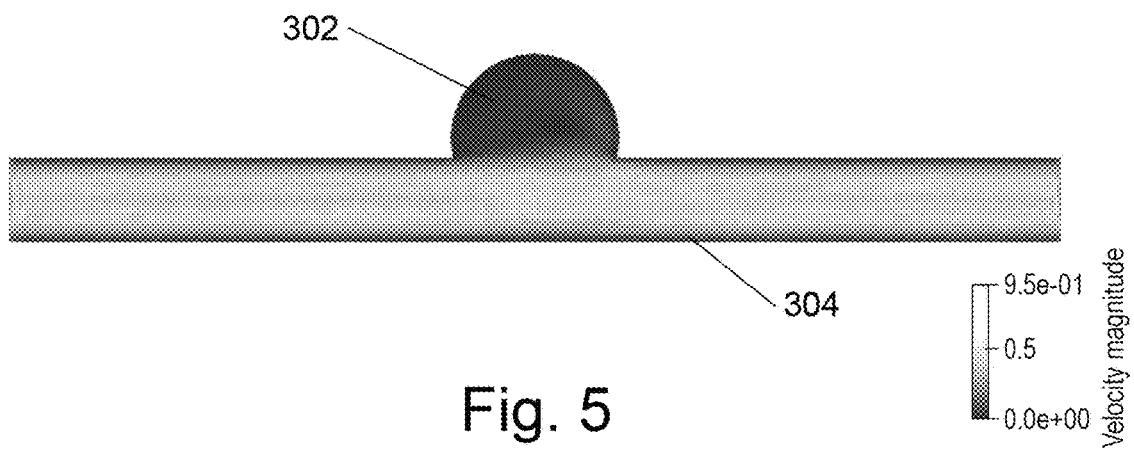
FIG. 5 shows magnitude of a reconstructed velocity field from projected velocity observations mapped onto a cross section of the example aneurysm of FIG. 3.
Figure 6:
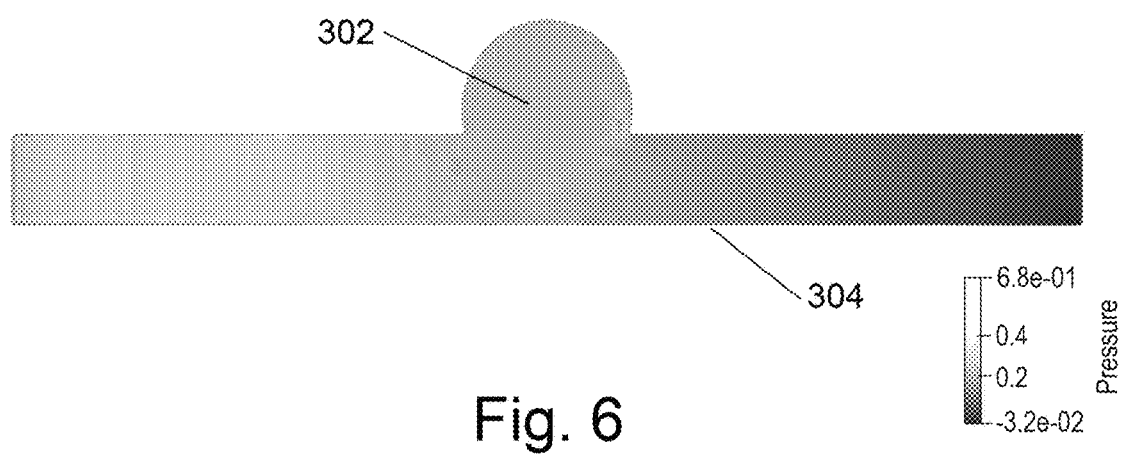
FIG. 6 shows a reconstructed pressure field from projected velocity observations mapped onto a cross section of the example aneurysm of FIG. 3.

After the neural network has been trained, then the 3D velocity and pressure fields can be determined, examples of which are shown in FIGS. 5 and 6 respectively. This determination includes processing the measurements of the one or more vector or tensor valued (e.g. velocity) fields projected onto one or more 2D acquisition planes to infer the data fields in 3D (e.g. the 3D velocity field) and/or can include the determination of properties such as pressure that are not directly observed. The 3D velocity field and pressure can in turn be used to derive clinical information such as fractional fluid reserve (FFR) and wall sheer stress.

Figure 7:
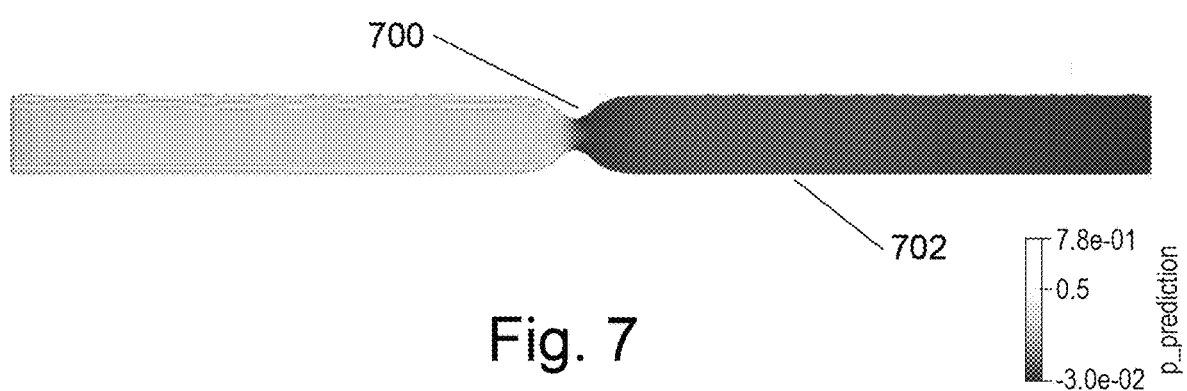
FIG. 7 is a single slice plot through an example stenosis showing pressure predicted using the process of FIG. 2.
Figure 8:
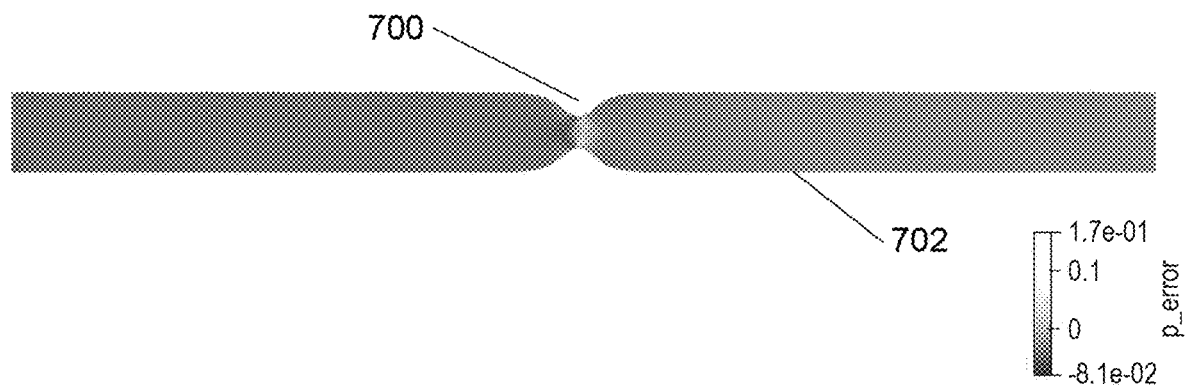
FIG. 8 is a single slice plot through the example stenosis illustrated in FIG. 7 showing error on the pressure predicted using the process of FIG. 2.
Figure 9:
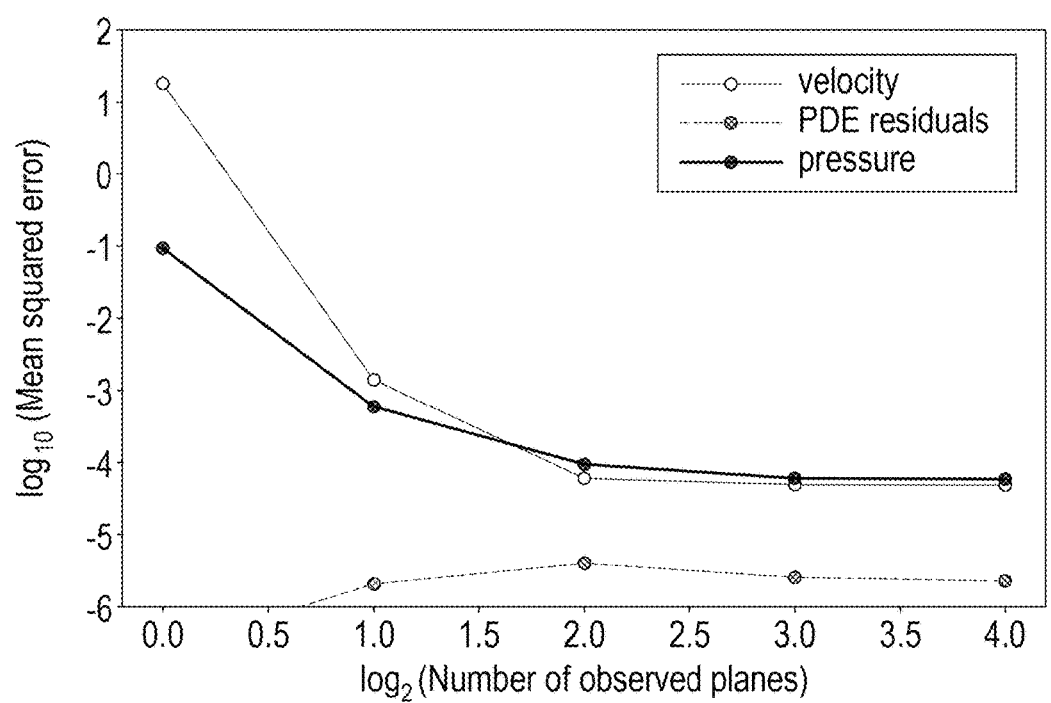
FIG. 9 is a plot of the variation of error with number of acquisition planes.

An example demonstrating the effectiveness of the process of FIG. 2 when applied to a stenosis 700 in a blood vessel 702 is illustrated in FIGS. 7 to 9. FIG. 7 shows a plot of pressure in a cross sectional slice through the blood vessel 702 as determined using the process of FIG. 2. As noted above the process involves measuring only projections of velocity of fluid flow (i.e. blood flow in this example) in 2D planes, and training a neural network that is subject to constraints defined by the Navier-Stokes or other equations representing the physical behavior of the system (i.e. of blood flowing in the blood vessel in this example). The measurements of projections of velocity of fluid flow can be collected using suitable physical measurement systems such as 2D Doppler ultrasound measurements or by using other suitable measurement systems such as phase contrast MRI, and the like. As noted above, if prior knowledge such as segmentation or other geometric or structural data of the blood vessel is available, then this can be used to set boundary conditions for the training of the neural network.

FIG. 8 shows the error on the prediction, which shows that the error is close to zero over most of the blood vessel 702.

FIG. 9 shows a plot of how the error in various properties, in this case velocity, pressure and the partial differential equation (PDE) residuals, varies with number of 2D planes for which measurement data is obtained. This shows that 3D fields, such as 3D velocity and pressure fields, can be derived from measurements of 2D projections of properties like velocity in only 2 to 4 2D planes with a low error.

As such, by applying the techniques described above, it may be possible to reduce measurement time as 3D data fields and non-measured properties can be derived from measurements of projections of properties in a low number of 2D planes. Furthermore, the application of the processes described herein potentially open up the use of different modalities, such as 2D Doppler ultrasound imaging, for use in situations where 3D data fields are required. This may allow more efficient utilization of equipment. Furthermore, the process can be used to generate data fields for properties that are not directly measured, for example, generating pressure data from 2D fluid velocity measurements.

Examples are given above that describe fluid velocity measurements being obtained using 2D Doppler ultrasound and used to determine 3D velocity and pressure fields, which are in turn used to determine clinical data such as FFR or shear wall stress. However, the present disclosure is not limited to this and the techniques described herein can be applied to other modalities, measurements and 3D data fields.

For example, ultrasound elastography could be used instead of 2D Doppler ultrasound. In particular, the ultrasound elastography could be used to obtain measurements of displacements projected onto one or more 2D planes and used with a physics informed neural network or other solution ansatz to determine 3D data fields indicative of elastic properties and/or stiffness of tissue. These in turn can be used to provide diagnostic information about the presence or status of disease affecting the tissue.

In another example, phase contrast MRI that measures fluid velocity projected onto 2D measurement fields can be used. Instead of three velocity measurement fields components being determined, the process can comprise collecting measurements of fluid velocity in only two out of three velocity field components. The process described above can then be applied to reconstruct a full 3D velocity field, and optionally also the pressure field.

In a further example, diffusion tensor imaging or diffusion weighted imaging can be used. In this case, the number of measurements of diffusion tensor components or the number of projections of measurements on 2D planes can be reduced. Equations describing anisotropic diffusion can be used as the constraining equations that are indicative of the underlying physical model. Any missing diffusion tensor components or projections of measurements on 2D planes can be inferred from the trained physics informed neural network that is subjected to the constraining equations representing the underlying physical model of the sample being analyzed.

Although several examples of modalities, measurements and 3D data planes are identified above, these are not intended to be limiting and others could be used.

In the examples above, a new neural network is initialized and trained. However, this need not necessarily be the case. For example, a pre-trained solution ansatz (e.g.

neural network) model can be used as a starting point, wherein the pre-trained neural network model was previously generated for a same or similar geometry or class of geometry or the same category of target as the target being imaged.

In another example, the solution ansatz arises from a numerical discretisation applied to the system of equations representative of the physical model describing underlying physical properties, for example the finite element or finite difference methods. The optimisation of the solution ansatz may comprise iteratively solving the system of equations, based on the measured 2D physical property data and parameters of the system of equations, to determine calculated 3D physical quantity data. Calculated 2D physical property data can then be determined from the calculated 3D physical property data. One or more parameters of the system of equations, such as initial condition, boundary conditions, fluid parameters, and the like, can be optimised by minimising a loss function representative of a difference between the calculated 2D physical quantity data and the measured 2D physical quantity data. This could comprise iteratively adjusting the one or more simulation parameters and determining new calculated 3D physical property data, re-calculating the loss function, and so on, using any suitable iterative minimisation techniques. In this approach, the system of equations representative of the physical model describing underlying physical properties is solved to within the error inherent to the numerical method, rather than being treated as another term in the loss function. This approach could optionally be performed as step 208 in FIG. 2 as part of the approach described above in respect to FIG. 2.

Method steps of the invention can be performed by one or more programmable processors executing a computer program to perform functions of the invention by operating on input data and generating output. Method steps can also be performed by special purpose logic circuitry, e.g., an FPGA (field programmable gate array) or an ASIC (application-specific integrated circuit) or other customised circuitry. Processors suitable for the execution of a computer program include CPUs and microprocessors, graphics processing units (GPU), maths co-processors, tensor processing units (TPU), and any one or more processors. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g. EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry. The computer will also be configured to communicate over a network, such as a local or wide area network, and/or over networks such as a wired, wireless or cellular network and optionally could communicate over the internet or by using a suitable data transfer protocol.

To provide for interaction with a user, the invention can be implemented on a device having a screen, e.g., a CRT (cathode ray tube), plasma, LED (light emitting diode) or LCD (liquid crystal display) monitor, for displaying information to the user and an input device, e.g., a keyboard, touch screen, a mouse, a trackball, and the like by which the user can provide input to the computer. Other kinds of devices can be used, for example, feedback provided to the user can be any form of sensory feedback, e.g., visual feedback, auditory feedback, or tactile feedback; and input from the user can be received in any form, including acoustic, speech, or tactile input. The individual features and/or combinations of features defined above in accordance with any aspect of the present invention or below in relation to any specific embodiment of the invention may be utilised, either separately and individually, alone or in combination with any other defined feature, in any other aspect or embodiment of the invention.

Furthermore, the present invention is intended to cover apparatus configured to perform any feature described herein in relation to a method and/or a method of using or producing, using or manufacturing any apparatus feature described herein.

Embodiments provide a medical image processing apparatus comprising processing circuitry configured to: receive measured 2D physical quantity data; determine 3D physical quantity data from the 2D physical quantity data using a model that is trained to transform 2D physical data into 3D physical data, the model being constrained by a system of equations representative of a physical model describing underlying physical properties. The 2D physical quantity data may comprise data obtained from medical imaging measurements. The 2D physical quantity data may comprise observations of one or more vector or tensor valued fields as projected from one or more 2D acquisition planes. The model may be comprised in a solution ansatz. The 3D physical quantity data may comprise a superset of 3D fields. The medical image processing apparatus may be configured to output the 3D physical quantity data.

The system of equations may be or comprise a system of partial differential equations. The solution ansatz may be differentiable with respect to space and/or time coordinates. The solution ansatz may comprise a neural network. A solution of the neural network may be constrained to obey said system of equations. The system of equations may be representative of a physical model, such as a physical model describing underlying physical properties of a target imaged by the medical imaging measurements. The neural network may be a physics constrained neural network. The equations may comprise Navier-Stokes equations or a reduced order approximation to Navier-Stokes equations. The equations may represent an arterial flow model in which a domain deforms with time.

The superset of 3D fields may comprise scalar, vector, or tensor fields. The solution ansatz for said fields may be differentiable with respect to the space and time coordinates. At least one of said vector or tensor valued field(s) may represent velocity.

The medical imaging measurements may comprise 2D Doppler ultrasound measurements or phase-contrast MRI measurements.

The processing circuitry may be configured to apply boundary conditions to training of the solution ansatz. The boundary conditions may be based on geometry or other prior knowledge of a target that is the subject of the medical imaging measurement. B-mode ultrasound measurements may be used to find vessel boundaries to be used as the boundary conditions. The medical imaging measurements may comprise projected velocity measurements obtained with 2D Doppler ultrasound. The processing circuitry may be configured to calculate clinically useful derived quantities, such as fractional flow reserve (FFR), using at least one of the 3D fields.

At least one of said vector or tensor valued field(s) may represent displacement. The equations may describe solid mechanics or elasticity. The processing circuitry may be configured to obtain physical parameters of a material. At least one of said vector or tensor valued field(s) may represent a diffusion tensor imaging data field. The equations may represent anisotropic diffusion.

The optimisation procedure may comprise a training process that includes loading a pre-trained model associated with a geometry of a system that is the subject of the medical imaging measurement.

The processing circuitry may be configured to use prior knowledge or segmentation to constrain a domain of possible solutions. The processing circuitry may be configured to infer a domain of possible solutions through the projected observations.

The processing circuitry may be configured to obtain the parameters of one or more of the acquisition planes via an optimisation method. The processing circuitry may be configured to obtain a line integral of one or more of the fields. The processing circuitry may be configured to obtain a point estimate of one or more of the fields. The processing circuitry may be configured to use the output to set the boundary/initial conditions of a fluid dynamics solver.

The training of the model may comprise determining 3D physical quantity data by inputting a plurality of the measured 2D physical quantity data to the model. The training of the model may comprise deriving determined 2D physical quantity data from the determined 3D physical quantity data. The training of the model may comprise generating a loss function representative of differences between the determined 2D physical quantity data and the measured 2D physical quantity data. The training of the model may comprise training the model based on data by minimizing the loss function. The training of the model may comprise varying one or more parameters of the model, re-determining 3D physical quantity data, re-determining 2D physical quantity data from the re-determined 3D physical quantity data, re-calculating the loss function and determining a value or change in the re-calculated loss function compared to a previously calculated loss function calculated using different parameters of the model.

The physical constraining of the model can be achieved, for example, by using an additional loss function that is representative of a degree by which the output of the neural network disobeys the equations representative of the physical model. This additional loss function can be constructed, for example, by combining derivatives of the neural network in such a way that they will sum to zero if the solution obeys the governing equations representative of the physical model.

Embodiments provide a medical image processing apparatus comprising processing circuitry configured to: obtain from medical imaging measurements, observations of one or more vector or tensor valued fields as projected onto one or more 2D acquisition planes; use an optimisation procedure to determine from the observations a superset of one or more 3D fields via a solution ansatz constrained by a system of equations, and output at least one of the 3D fields.

Embodiments provide a medical imaging method comprising receiving measured 2D physical quantity data; and determining 3D physical quantity data from the 2D physical quantity data using a model constrained by a system of equations representative of a physical model describing underlying physical properties and that is trained to transform 2D physical data into 3D physical data.

Embodiments provide a medical imaging method that comprises obtaining from medical imaging measurements, observations of one or more vector or tensor valued fields as projected from one or more 2D acquisition planes; using an optimisation procedure to determine from the observations a superset of 3D fields via a solution ansatz constrained by a system of partial differential equations, and outputting the plurality of these fields.

Embodiments provide a method of training a model for use in medical image processing the model being constrained by a system of equations representative of a physical model describing underlying physical properties and configured to receive measured 2D physical quantity data and determine 3D physical quantity data from the 2D physical quantity data, the method comprising: determining 3D physical quantity data by inputting a plurality of the measured 2D physical quantity data to the model; deriving determined 2D physical quantity data from the determined 3D physical quantity data;

generating a loss function representative of differences between the determined 2D physical quantity data and the measured 2D physical quantity data; and training the model based on data by minimizing the loss function.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments are described, these embodiments have been presented by way of example only, and are not intended to limit the scope of the invention. Indeed, the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:
1. A medical image processing apparatus, comprising:
processing circuitry configured to receive measured 2D physical quantity data, wherein the 2D physical quantity data was obtained from medical imaging measurements, and comprises observations of one or more vector- or tensor-valued fields as projected from one or more 2D acquisition planes; and determine 3D physical quantity data from the measured 2D physical quantity data using a model that was trained to predict a 3D data field, wherein the predicting training of the 3D data field model comprises minimizing differences between a 2D projection of the 3D data field and the measured 2D physical quantity data, the model following or being constrained by a system of equations representative of a physical model describing underlying physical properties.

2. The medical image processing apparatus according to claim 1, wherein:

the model is based on a solution ansatz;

the 3D physical quantity data comprises a superset of 3D fields; and the medical image processing apparatus is configured to output the 3D physical quantity data.

3. The medical image processing apparatus according to claim 2, wherein the solution ansatz comprises a neural network and the neural network is constrained to obey the system of equations.

4. The medical image processing apparatus according to claim 3, wherein the system of equations is representative of the physical model describing the underlying physical properties, which are associated with a target imaged by the medical imaging measurements, and the neural network is a physics constrained neural network.

5. The medical image processing apparatus according to claim 2, wherein the solution ansatz arises from a numerical discretization applied to the system of equations representative of the physical model describing underlying physical properties and an optimization of the solution ansatz comprises iteratively solving the system of equations to determine calculated 2D physical quantity data and minimizing a loss function representative of a difference between the calculated 2D physical quantity data and the measured 2D physical quantity data by adjusting one or more simulation parameters.

6. The medical image processing apparatus according to of claim 2, wherein the processing circuitry is configured to:

use prior knowledge or segmentation to constrain a domain of possible solutions;

infer a domain of possible solutions through the projected observations;

obtain parameters of one or more of the 2D acquisition planes via an optimization method;

obtain a line integral of one or more of the fields;

obtain a point estimate of the one or more of the fields; and use the output to set at least one of boundary and initial conditions of a fluid dynamics solver.

7. The medical image processing apparatus according to claim 1, wherein the measured 2D physical quantity data comprises data representing velocity.

8. The medical image processing apparatus according to claim 1, wherein, the measured 2D physical quantity data comprises 2D Doppler ultrasound measurements or phase-contrast MRI measurements.

9. The medical image processing apparatus according to claim 1, wherein the processing circuitry is further configured to apply boundary conditions to training of the model, the boundary conditions being based on geometry or other prior knowledge of a target that is a subject of the 2D physical quantity data.

10. The medical image processing apparatus according to claim 9, wherein B-mode ultrasound measurements are used to find vessel boundaries to be used as the boundary conditions, and the measured 2D physical quantity data comprises projected velocity measurements obtained using 2D Doppler ultrasound.

11. The medical image processing apparatus according to claim 1, wherein:

the system of equations comprises partial differential equations;

the system of equations represent an arterial flow model in which a domain deforms with time; and the processing circuitry is further configured to calculate clinically useful derived quantities using the 3D physical data.

12. The medical image processing apparatus according to claim 1, wherein the measured 2D physical quantity data comprises data representative of displacement.

13. The medical image processing apparatus according to claim 12, wherein the system of equations describes at least one of solid mechanics and elasticity.

14. The medical image processing apparatus of claim 12, wherein the processing circuitry is further configured to obtain physical parameters of a material.

15. The medical image processing apparatus according to claim 1, wherein the measured 2D physical quantity data comprises data representative of diffusion tensor imaging data.

16. The medical image processing apparatus according to claim 15, wherein the system of equations represents anisotropic diffusion.

17. The medical image processing apparatus according to claim 1, wherein the model is optimized, and the optimization of the model comprises a training process that includes loading a pre-trained initial model associated with a geometry of a target that is a subject of the medical imaging measurement.

18. The medical image processing apparatus according to claim 1, wherein training of the model comprises:

determining the 3D physical quantity data by inputting a plurality of the measured 2D physical quantity data to the model, deriving the 2D projection from the determined 3D physical quantity data;

generating a loss function representative of differences between the derived 2D projection and the measured 2D physical quantity data; and training the model based on data by minimizing the loss function.

19. A medical imaging method, comprising:

receiving measured 2D physical quantity data, wherein the 2D physical quantity data was obtained from medical imaging measurements, and comprises observations of one or more vector- or tensor-valued fields as projected from one or more 2D acquisition planes; and determining 3D physical quantity data from the measured 2D physical quantity data using a model constrained by a system of equations representative of a physical model describing underlying physical properties and that was trained to predict a 3D data field, wherein the training of the model comprises minimizing differences between a 2D projection of the 3D data field and the measured 2D physical quantity data.

20. A method of training a model for use in medical image processing, the model being constrained by a system of equations representative of a physical model describing underlying physical properties and configured to receive measured 2D physical quantity data, wherein the 2D physical quantity data was obtained from medical imaging measurements, and comprises observations of one or more vector- or tensor-valued fields as projected from one or more 2D acquisition planes, and determine 3D physical quantity data from the 2D physical quantity data, the method comprising:
- predicting a 3D data field using the model, from measured 2D physical quantity data;
- deriving a 2D projection of the 3D data field;
- generating a loss function representative of differences between the derived 2D projection and the measured 2D physical quantity data; and
- training the model based on data by minimizing the loss function.

* * * * *